(12) United States Patent
Reetz et al.

(10) Patent No.: US 6,982,247 B1
(45) Date of Patent: Jan. 3, 2006

(54) COMPOUNDS EXHIBITING AN ANTIBIOTIC ACTIVITY

(75) Inventors: Manfred T. Reetz, Mülheim an der Ruhr (DE); Klaus Kühling, Ludwigshafen (DE); Heinz Mehlhorn, Düsseldorf (DE); Karl-Erich Jäger, Mülheim an der Ruhr (DE)

(73) Assignee: B.R.A.I.N., Zwingenberg (DE)

( * ) Notice: Subject to any disclaimer, the term of this patent is extended or adjusted under 35 U.S.C. 154(b) by 0 days.

(21) Appl. No.: 09/979,672

(22) PCT Filed: May 6, 2000

(86) PCT No.: PCT/EP00/04089

§ 371 (c)(1),
(2), (4) Date: Nov. 5, 2001

(87) PCT Pub. No.: WO00/68258

PCT Pub. Date: Nov. 16, 2000

(30) Foreign Application Priority Data

May 7, 1999 (DE) ................................ 199 21 027

(51) Int. Cl.
*A61K 38/14* (2006.01)
*C07K 14/435* (2006.01)

(52) U.S. Cl. ............................... 514/2; 514/12; 514/13; 514/14; 530/350; 530/395; 530/402; 424/278.1; 435/888; 930/190

(58) Field of Classification Search ............... 530/350, 530/395, 402; 514/12, 13, 14, 2; 424/278.1; 435/888; 930/190
See application file for complete search history.

(56) References Cited

OTHER PUBLICATIONS

Takamatsu, N. et al. (1995) Molecular cloning of the defense factor in the albumen gland of the sea hare Aplysia kurodia. FEBS Lett., vol. 377, pp. 373-376.*

* cited by examiner

*Primary Examiner*—Karen Cochrane Carlson
*Assistant Examiner*—Samuel W. Liu
(74) *Attorney, Agent, or Firm*—Norris McLaughlin & Marcus PA

(57) ABSTRACT

The present invention relates to compounds having antibiotic activity which are obtained from body fluids of mollusks, namely of certain West-African snails, to therapeutic drugs comprising these compounds, and to the use thereof for the preparation of a therapeutic drug for controlling infectious pathogens in humans and animals.

11 Claims, 4 Drawing Sheets

Fig. 1/4
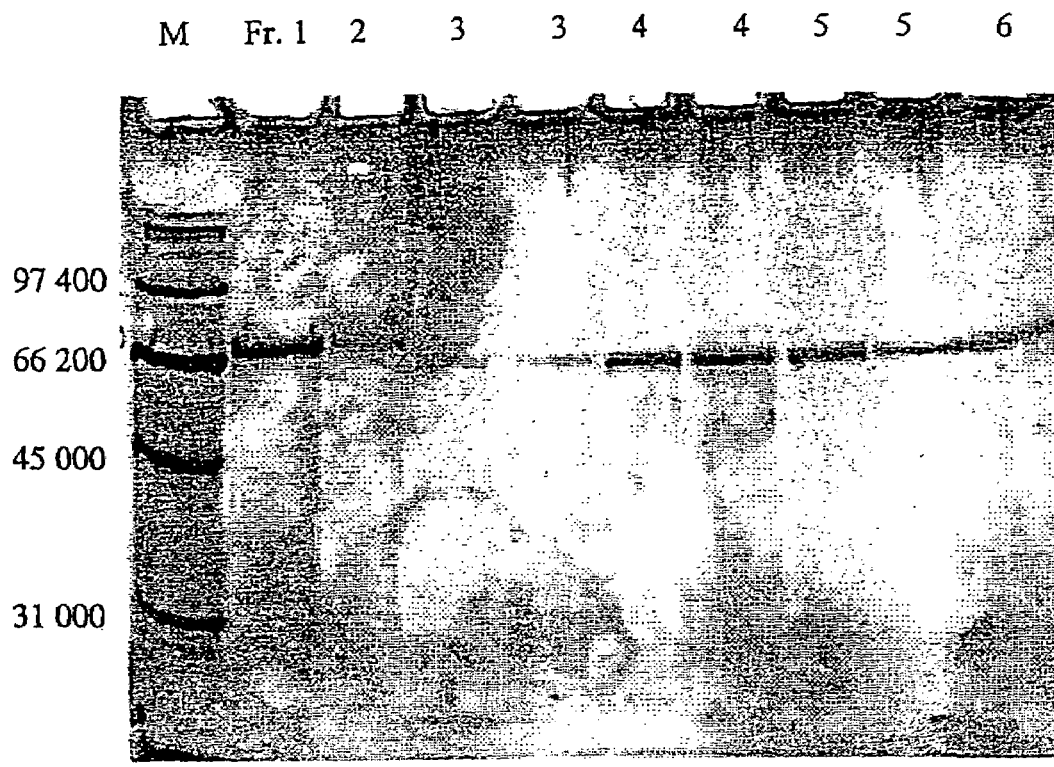

Fig. 2/4

```
                    1
Achacin             mlllnsalfilclvcwlpgtsssrvltrregpqcsrsvdvavvgagpsgtysayklrnkgqtv 64
Achacin             elfeysnriggrlftthlpnvpdlnlesggmryfknhhkifgvlvkelnlsnkeftegfgkpg 127
Achacin             rtrffargksltleemtsgdvpynlsteekanqanlagyylkkltgfdgevltipqanklevd 190
Achacin             dgrklyqltvdealdkvgtpegkeflkafstgntefiegvsavnyflvelgereeeiltltdg 253
Achacin             msalpqaladaflksstshaltlnrklqslsktdnglyllefletnthegyteesnitdlvca
Konsensus                                       td+glyllefl+t.t++g..+e+.i.   v..
Peptid 1/2                                      tdtglylleflhtftedgsiqetgik   vil
                    316
Achacin             rkvilaipqsalihldwkplrsetvneafnavkfiptskvfltfptawwlsdavknpafvvks
Konsensus           ..+..a+.+.....l+                         ..tfpt.+ +.+.
Peptid 2/6          aipqsalieldwkplr.                        dntfpttyvaeek
                    379
Achacin             tspfnqmydwkssnvtgdaamiasyadtsdtkfqenlnskgelipgsapganrvtvalkeell
Konsensus                                            qenln.+ge, ipgsapganr
Peptid 3                                           qenlnaqgepipgsapganr
                    442
Achacin             sqlsqaygiersdipepksgtsqfwssypfegdwtvwkagyhceytcyiierpsliddvfvvg
Konsensus                                             agyhc+y..yii+r
Peptid 4                                            agyhcqyiiyiiqr
                    505                        531
Achacin             sdhvncienawtesaflsvenvfekyf
```

Fig. 3/4

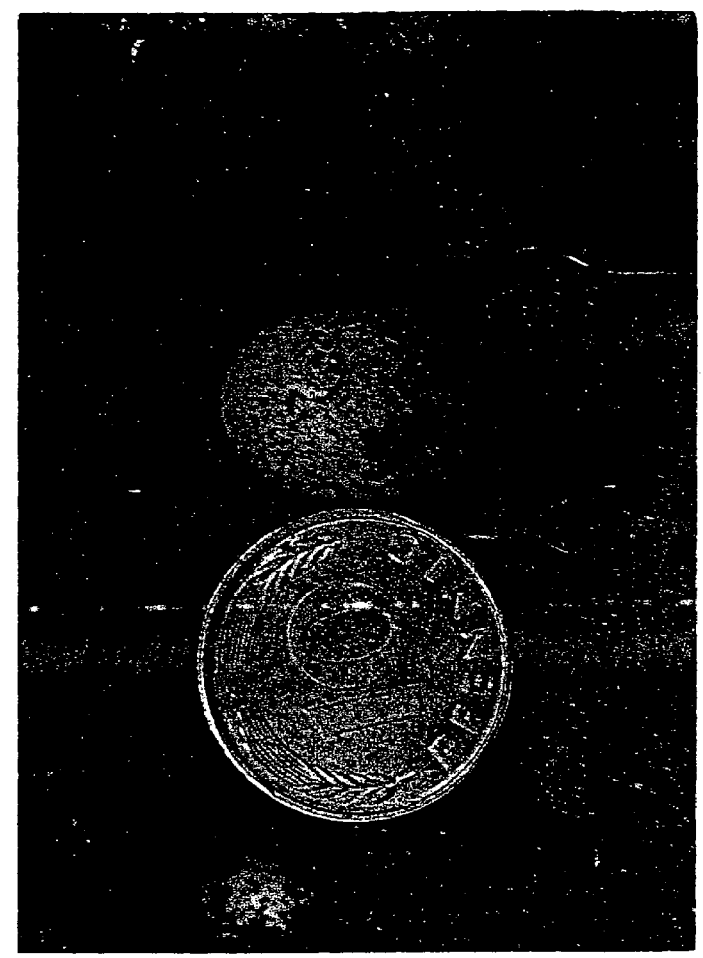
Fig. 4/4

COMPOUNDS EXHIBITING AN ANTIBIOTIC ACTIVITY

This application is a 371 of PCT/EP00/04089 filed 6 May 2000, which claims foreign priority benefit of the filing date under 35 U.S.C. 119 of Germany patent application No. 19921027.6 filed 7 May 1999.

The present invention relates to compounds having antibiotic activity which are obtained from body fluids of mollusks, namely of certain West-African snails, to therapeutic drug comprising these compounds, and to the use thereof for the preparation of a therapeutic drug for controlling infectious pathogens in humans and animals.

BACKGROUND OF THE INVENTION

A general strategy for controlling infectious pathogens in humans and animals is the application of antibiotics, of which several thousand different compounds have been isolated and used to date. However, as a rule, their antibiotic activity is limited to only a few closely related pathogen species. In addition, an increasingly growing problem in the use of antibiotics is the occurrence of resistant bacteria [J. Davies, Science 1994, 264, 375–382; Inactivation of antibiotics and the dissemination of resistance genes]. The spreading of resistant bacteria takes from 2 to 5 years as a rule, so that there is a strong need to find or develop new efficient antibacterially effective agents. Attempts are also made to recover and employ so-called natural antibiotics; these are peptides or proteins which can be recovered from those organisms which come into contact with bacteria, i.e., from plants, lower and higher animals and humans. Although some natural antibiotics have been isolated and characterized, it has not been successful to date to develop them further to clinical use [J. E. Gabay, Science 1994, 264, 373–374; Ubiquitous natural antibiotics].

Now, it has surprisingly been found that compounds having antibiotic activity can be recovered from certain West-African snail species, namely snails of the genus *Archachatina* (especially the species *A. marginata, A. degneri* and *A. ventricosa*) and members of the genus *Achatina* with the species *A. achatina, A. monochromatica* and *A. batteata*. Inter alia, a protein isolated and identified from the yellowish mucus of the foot soles of these snails can be employed against a broad range of infectious pathogens.

SUMMARY OF THE INVENTION

Thus, the present invention relates to
(1) compounds having antibiotic activity which can be isolated from body fluids of snails of the genus *Archachatina* and/or the species *Achatina achatina, Achatina monochromatica* and *Achatina batteata* of the genus *Achatina*;
(2) in a preferred embodiment, the compounds (1) are a peptide, protein or derivative thereof;
(3) a DNA sequence coding for a peptide, protein or derivative thereof according to item (2);
(4) a vector comprising a DNA sequence according to item (3);
(5) a host organism transformed with a vector according to item (4) and/or comprising a DNA sequence according to item (3);
(6) a process for the preparation of the peptide, protein or derivative thereof according to item (2), comprising culturing a host organism according to item (5) and isolating the peptide, protein or derivative thereof;
(7) a therapeutic drug containing a compound according to item (1) or (2) and optionally a pharmaceutically acceptable carrier material;
(8) use of a compound according to item (1) or (2) for the preparation of a therapeutic drug for controlling infectious pathogens in humans and animals;
(9) a foodstuff or feed, containing a compound according to item (1) or (2); and
(10) a method for treating infectious pathogens in humans and animals, comprising administering a compound according to item (1) or (2).

DESCRIPTION OF FIGURES

FIG. 1: Determination of the molecular weight of the antibiotically effective substance with polyacrylamide gel electrophoresis (SDS-PAGE). Beside the size standard (M) in lane 1, the individual fractions of the ion-exchange chromatography have been applied in lanes 2 to 10. It is clearly seen that a higher-molecular weight protein is eluted first (fractions 1 and 2), followed by the antibacterially effective substance (fractions 3 to 6), which occurs in a pure form and in the highest concentration in fraction 4.

FIG. 2: Comparison of the amino acid sequences of five peptides from the antibacterially effective protein from *Archachatina marginata* with that of the antibacterially effective protein achacin from *Achatina fulica*. The consensus sequences are stated between the amino acid sequences of achacin and those of the peptides; identical amino acids are stated in the one-letter code, similar ones are marked with a positive sign, different ones with a period.

FIG. 3: Snail of the genus *Archachatina*, i.e., *Archachatina marginata*.

FIG. 4: Eggs of *Archachatina marginata*.

DETAILED DESCRIPTION OF THE INVENTION

The antibiotically effective substances are produced by snails of the genus *Archachatina* (especially the species *A. marginata, A. degneri, A. ventricosa*) and members of the genus *Achatina* with the species *A. achatina, A. monochromatica* and *A. batteata*. The distribution of these land snails, which have a size of up to 15 cm, in West Africa has been described by Hodashi [J. K. M. Hodashi, Revue mondiale de Zootechnie 1984, 52, 24–35; Les escargots géants comestibles d'Afrique occidentale]. Outwardly, the shells of the snails of the genera *Archachatina* and *Achatina* can be distinguished by the shape of the shell apex, *Achatina* having a pointed apex while *Archachatina* has a blunt apex. A further distinctive feature is the size of the eggs: *Achatina* deposits many eggs sized about 3–4 mm while *Archachatina* deposits only a few eggs sized about 1 cm (see FIG. 4). The snails are vegetarians and can be bred in laboratories, which ensures their availability.

Active substances which can be recovered from these snails include:
1. yellowish mucus from the foot sole, to be recovered by scalpel scraping or by stimulation with current pulses of 0.5 to 1 mA;
2. whitish to bluish defense secretion, to be recovered upon applying a small injury with a scalpel; the snail will release this secretion in a thick jet from the mantle cavity;
3. reddish hemolymph which exits from the body cavity upon injury;
4. shell powder, to be recovered by grinding the shell.

Most effective according to the invention is a peptide, protein or derivative thereof which is a component of the yellowish mucus from the foot sole of the mentioned snail, in particular, derived from *Archachatina marginata* (see FIG. 3). The column-chromatographic purification using the following process steps:

(a) repeated ultrafiltration;

(b) gel permeation chromatography; and (c) ion-exchange chromatography;

to electrophoretic homogeneity yielded a fraction which showed one band in SDS-PAGE (FIG. 1) whose intensity correlated with biological effectiveness. Therefore, the antibacterially effective compound is preferably a protein or protein derivative having an apparent molecular weight of about 60 kDa. This result is in accordance with the results obtained by ultrafiltration of the effective compound, i.e., that the molecular weight of the searched substance must be greater than 50 kDa.

The protein or protein derivative according to the present invention preferably comprises at least one, especially all eight, of the partial sequences shown in Table 1.

TABLE 1

Amino acid sequences of peptides from an antibacterially effective protein from the snail *Archachatina marginata*

| | |
|---|---|
| Peptide 1 TDTGLYLLEFLHTFTEDGSIQETGIK | (26 amino acids; SEQ ID NO:1) |
| Peptide 2 VILAIPQSALIELDWKPLR | (19 amino acids; SEQ ID NO:2) |
| Peptide 3 QENLNAQGEPIPGSAPGANR | (20 amino acids; SEQ ID NO:3) |
| Peptide 4 AGYHCQYIIYIIQR | (14 amino acids; SEQ ID NO:4) |
| Peptide 5 QEQNGNLMYLNR | (12 amino acids; SEQ ID NO:5) |
| Peptide 6 DNTFPTTYVAEEK | (13 amino acids; SEQ ID NO:6) |
| Peptide 7 IFDDKPIPVAQDETK | (15 amino acids; SEQ ID NO:7) |
| Peptide 8 TNAEYEFLTTFRLNAYK | (17 amino acids; SEQ ID NO:8) |

The partial sequences of eight peptides from the effective protein shown in Table 1 were aligned with the amino acid sequences present in the accessible protein data bases (SwissProt, EMBL, NCBI). Only a slight similarity to the protein achacin from the snail *Achatina fulica* Férussac (Obara, 1992; Accession No. P35903) could be established, i.e., that on average only 35% of the amino acids compared from both proteins are identical (see FIG. 2). Of 136 amino acids sequenced to date, 88 are different, as can be seen from the following Table 2.

TABLE 2

| Snail peptides | Length of sequence [amino acids] | differing amino acids[1.)] (including similar ones) | Identity[2.)] [%] |
|---|---|---|---|
| Peptide 1 | 26 | 11 | 58 |
| Peptide 2 | 19 | 16 | 16 |
| Peptide 3 | 20 | 3 | 85 |
| Peptide 4 | 14 | 4 | 71 |
| Peptide 5 | 12 | 13 | — |
| Peptide 6 | 13 | 9 | 31 |

TABLE 2-continued

| Snail peptides | Length of sequence [amino acids] | differing amino acids[1.)] (including similar ones) | Identity[2.)] [%] |
|---|---|---|---|
| Peptide 7 | 15 | 15 | — |
| Peptide 8 | 17 | 17 | — |
| TOTAL: | 136 | 88 | 35 |

[1.)]differing amino acids comprise conservative substitutes (e.g., E/H; E/Q; S/T; V/P)
[2.)][%] amino acids identical with those of achacin isolated from *Achatina fulica*

Further homologies with previously known proteins were not found. Thus, the antibiotically effective compounds of the present invention are not identical with the substances described in the literature from the land snail *Achatina fulica* from Okinawa (referred to as achacin) [H. Otsuka-Fuchino, Y. Watanabe, C. Hirakawa, T. Tamiya, J. J. Matsumoto, T. Tsuchiya, Comp. Biochem. Physiol. 1992, 101C(3), 607–613; Bactericidal action of a glycoprotein from the body surface mucus of giant African snail; Y. Kubota, Y. Watanabe, H. Otsuka, T. Tamiya, T. Tsuchiya, J. J. Matsumoto, Comp. Biochem. Physiol. 1985, 82, 345–348; Purification and Characterization of an Antibacterial Factor from Snail Mucus; K. Obara, H. Otsuka-Fuchino, N. Sattayasai, Y. Nonomura, T. Tsuchiya, T. Tamiya, Eur. J. Biochem. 1992, 209, 1–6; Molecular cloning of the antibacterial protein of the giant African snail, *Achatina fulica* Férussac] and from the Japanese aquatic snail *Aplysia kurodai* (referred to as *aplysienin A*) [N. Taka-matsu, T. Shiba, K. Muramoto, H. Kamiya, FEBS Letters 1995, 377, 373–376; Molecular cloning of the defense factor in the albumen gland of the sea hare *Aplysia kurodai*].

The mucus containing the active compound (i.e., the peptide, protein or derivative thereof) is stable upon storage at from −80° C. up to +40° C. and does not lose its pharmacological and antibacterial activities. Also, the antibacterial activity was not adversely affected by storage at room temperature at pH 8 or pH 9.5. Upon heating at above 70° C. or 110° C. for 30 min, the activity is completely lost. Both the purified substance and the isolated raw mucus can be lyophilized and reconstituted in water without losing the above described activity. Fractions fivefold concentrated in this manner exhibited inhibition halos with diameters of up to 1.6 cm. Solubility experiments showed that the searched substance dissolves in water, but not in methanol, hexane or a chloro-form/methanol mixture (4:1).

In addition to the substances directly obtained from the above mentioned snails in a non-purified or purified form, useful effective substances include all kinds of modified variants, which are obtained, for example, from proteins by the chemical modification of amino acids including glycosylation, ribosylation, acylation, phosphorylation and others. Also effective are those modified variants which are obtained by genetic engineering methods. These include those modified variants which are obtained by employing DNA molecules which code for the substance described and have been subjected to mutagenesis by a molecular-biological technique (e.g., chemical, site-directed or random mutagenesis, also with methods of PCR, methods of directed evolution, staggered extension process, DNA shuffling etc. [M. T. Reetz, K.-E. Jaeger, Top. Curr. Chem. 1999, 200 (Biocatalysis), 31–57; Superior biocatalysts by directed evolution]) for the recombinant techniques described in the following.

As a rule, the above described substances are processed, prepared and/or purified in different processes adapted to the respective application.

The present invention also relates to DNA sequences which code for the above defined peptides, proteins or derivatives thereof (including partial sequences, such as those shown in Table 1). These DNA sequences can be introduced into suitable expression vectors, and a suitable host organism can be transformed with these vectors, or host organisms can be transfected with the mentioned DNA sequences. The transformed/transfected host organisms can then be used for the preparation of the desired peptide, protein or derivative. Suitable host organisms according to the present invention include microorganisms, such as bacteria (e.g., *E. coli*), and yeasts and mammal cell systems, such as CHO cells and immortalized mammal cells.

The antibiotically effective compounds according to the present invention can kill bacteria, parasites, viruses and other infectious pathogens upon both external and internal administration. The infectious pathogens against which the compounds according to the invention are effective are those which cause gastro-intestinal symptoms, those which attack inner organs via the blood, and those which lead to open wounds in the skin.

Thus, the antibacterial effectiveness of the protein isolated from *Archachatina marginata* having an apparent molecular weight of about 60 kDa could be shown by a bioassay using bacterial isolates freshly isolated from infected and hospitalized patients. An antibacterial-bactericidal effect was established, inter alia, against the Gram-negative species *Escherichia coli* and *Pseudomonas aeruginosa*, and the Gram-positive species *Staphylococcus aureus* and *Staphylococcus epidermidis* (see Examples 3 and 4).

The above mentioned protein is also effective against other infectious pathogens. Examples which may be mentioned include malarial parasites of the genus *Plasmodium* (various species). In the test system described in Example 5, the administration of the substance to malaria-infected mice resulted in a significantly increased survival rate as compared with an untreated control group.

The therapeutic drug according to the invention can be present in the following dosage forms:
a) oral as a solution (sterile-filtered and optionally diluted with water), e.g., for curing infections of the gastrointestinal tract (e.g., gastritis);
b) application as a solution (as in a)) into open wounds for wound healing or the killing of bacteria or other pathogens in the blood stream (e.g., for preventing a sepsis);
c) administration of isolated, purified and optionally formulated fractions in the forms and with the objectives as in a) and b);
d) administration in the form as in c), but as a lyophilizate (e.g., for application to open wounds for wound healing).

The invention also relates to therapeutic drugs which contain the substances according to the invention and can be employed for controlling bacterioses and other infectious pathogens in humans and animals.

Therapeutic drugs for oral administration can be powders, granules, emulsion or suspension concentrates, which may be administered to humans or animals alone or mixed with food. Such therapeutic drugs can be prepared by analogy with conventional methods, for example, by mixing the active substance (entirely or in fractions) with solid or liquid carrier materials, optionally with the addition of additives, such as excipients, emulsifying or dispersing agents, solvents, dyes, preservatives and/or antioxidants. Suitable solvents include, for example, distilled water and physiological saline; suitable preservatives include, for example, benzyl alcohol, benzalkonium chlorides and phenol; and suitable excipients include, for example, carboxymethylcellulose and sodium alginate.

The same applies, mutatis mutandis, to therapeutic drugs for topical administration. The above statements also apply when agents containing the active sub-stance are employed in the blood stream (intravenous administration).

Due to the high potency of the present compounds (activity already in the femto-molar range), small quantities of the compound are sufficient for achieving the desired therapeutical effect. However, the daily dose of the compound according to the invention is dependent on the therapeutical object, the physical constitution of the patient, and the dosage form. Thus, the daily dose for oral and topical administration is within a range of from 0.01 mg to 10 g, preferably from 1 mg to 1 g, and for intravenous administration, it is within a range of from 1 $\mu$g to 10 g, preferably from 0.1 mg to 1 g.

The invention also relates to food and feed additives which contain the pure or fractioned substances from snails of the genera *Achatina* and *Archachatina* or from reproductive systems and are suitably mixed with the foodstuffs or with the special feed for various animal species. The optimum effective dose for the treatment of infections with the mentioned bacteria or infectious pathogens depends on the bacterial or pathogenic species, the nature and duration of the treatment, and the age and condition of the humans and animals being treated.

The method for treating the above mentioned symptoms in humans and animals includes a method for the treatment of malaria in humans.

The present invention will be further illustrated by the following Examples.

EXAMPLES

Example 1

Isolation and Purification

The yellow mucus isolated from the foot sole of the snail *Archachatina marginata* was purified by several ultrafiltration steps. After prefiltration through a membrane having a pore size of 0.65 $\mu$m, the filtrate was applied to a membrane with the next smaller exclusion threshold. Membranes of Millipore/Amicon having the following exclusion thresholds (kDa) were used: 100, 50, 30, 10 and 5. Optionally, a centrifugation may be performed for 1 h at 31,000×g (centrifuge Sorvall R2/5B, rotor SS34, 20,000 rpm), the solid components contained in the mucus forming a pellet. The supernatant was diluted with one volume equivalent of buffer solution (10 mM Tris/100 mM NaCl, pH 8) and further purified by gel permeation chromatography (GPC) followed by ion-exchange chromatography. As the separating column for the preparative GPC separation, a Fractogel EMD BioSEC column (length: 600 mm, inner diameter: 15 mm, Merck) was used. The elution buffer consisted of 10 mM Tris/100 mM NaCl, pH 8; elution was effected at a flow rate of 1 ml/min under a pressure of 2.0 MPa. Detection was effected by spectral photometry at 210 nm. For the ion-exchange chromatographic separation of the concentrated GPC fractions, a UNO Q6 column (length: 53 mm, inner diameter: 12 mm, BioRad) was used. The elution buffer consisted of 10 mM Tris/100 mM NaCl, pH 9.5; elution was effected at a flow rate of 2 ml/min under a pressure of 3.8 MPa. Detection was effected by spectral photometry at 210 nm. The purity of the fractions obtained was checked by SDS polyacrylamide gel electrophoresis (SDS-PAGE) followed by silver staining of the gels.

Example 2

Determination of the Amino Acid Sequences of Tryptic Peptides

The peak fractions from the column-chromatographic separation having the highest biological activity were concentrated by ultrafiltration through Centricon 30 (Amicon). The protein was mixed with 5 M guanidine hydrochloride, carboxy-methylated over night and dialyzed using a microdialysis apparatus (Pierce). The carboxymethylated protein (12 µg) was tryptically digested over night (ratio of 1 part of protein:5 parts of trypsin). The peptides were separated by HPLC on a reversed-phase column (C-18, 300 µm, length: 25 cm). The protein content of the fractions was detected by spectral photometry at 295 and 215 nm, and a MALDI mass spectrum was recorded from selected fractions. After evaluation of the spectra, 8 peptides were selected and subjected to high sensitive microsequencing on a ProSize 494 Sequencer (Perkin Elmer—Applied Biosystems). The sequences of the peptides are summarized above in Table 1.

Example 3

Determination of Antimicrobial Activity I

The antibacterial activity of the fractions obtained in Example 1 was examined by a bioassay. Thus, a culture of the human-pathogenic bacterium *Staphylococcus aureus* in complete medium (NB, Difco) was incubated at 37° C. with shaking for 3–4 h until the bacteria had reached a cell density of about $5\times10^8$ ml$^{-1}$ (logarithmic growth phase). Of this culture, 100 µl each was applied to NB agar plates by plating with a spatula and allowed to stand at room temperature for about 30 min, followed by pipetting aliquots of the fractions (volume: 5 or 10 µl) onto the plate. The plates were incubated at 37° C. over night, and the biological activity evaluated by determining the diameter of the inhibition halos formed on the bacterial lawn; it was about 10 to 16 mm for the active fractions. The results are summarized in Table 3.

TABLE 3

| Bacterial strain[1] | Gram classification | Activity of the extract[2,3] |
|---|---|---|
| *Escherichia coli* | negative | + |
| *Pseudomonas aeruginosa* | negative | + |
| *Staphylococcus aureus* | positive | ++ |
| *Staphylococcus epidermidis* | positive | ++ |

[1]The bacterial strains tested are clinical isolates derived from infected patients.
[2]For the tests, there was used 10 µl each of snail extract applied to an agar plate which had previously been inoculated with a suspension of the respective bacterium.
[3]The symbols mean the following inhibition halo diameters: + means 0.9 to 1.2 cm; ++ means 1.3 to 1.6 cm.

Assuming a molecular weight of 60,000 for the active protein, this means that the application of 460 femtomoles ($4.6\times10^{-13}$ mol) of the substance is sufficient to achieve complete inhibition of bacterial growth (diameter of the inhibition halo: 1.4 cm) in vitro.

Example 4

Determination of Antimicrobial Activity II

Materials and Methods:

The antibiotically active protein isolated in Example 1 was provided in a buffer solution (10 mM Tris, 100 mM NaCl, pH 9.5). The protein content of the solution was 1000 µg/ml.

To examine the antimicrobial activity of the protein, determinations of the minimum inhibitory concentration (MIC) were effected using the microdilution technique according to DIN 58940 for *Staphylococcus aureus* (including MRSA), Enterobacteriaceae (including cefotaxim-resistant strains), non-fermenters (especially *Pseudomonas aeruginosa*) and *Candida albicans*. Thus, the buffered protein solution was added to sterile Mueller-Hinton broth (pH 7.4) in serial dilutions of geometric relationship with factor 2. The range of concentration examined was from 0.03 to 32 mg/l. After about 20 hours of incubation at 37° C., the MIC values were read.

For quality control, ATCC reference strains were also tested: *S. aureus* ATCC 25923, *S. aureus* ATCC 29213, *E. coli* ATCC 25922, *E. coli* ATCC 35218 and *P. aeruginosa* ATCC 27853.

Results:

A total of 77 isolates from human-medical test samples were examined: 45 *Staphylococcus aureus*, including 33 methicillin-resistant or multiresistant (MRSA); 14 non-fermenters, including 12 *Pseudomonas aeruginosa;* 13 Enterobacteriaceae, including 9 *Escherichia coli*, in part cefotaxim-resistant, and 5 *Candida albicans*. All MIC values could be easily read, i.e., there were sharp end points.

The individual MIC values are listed in Tables 4a and 4b. A summary of the results is found in Table 5.

1. The MIC values for all *Staphylococcus aureus* isolates are between 0.125 and 0.5 mg/l, methicillin-resistant isolates (MRSA) rather having a higher sensitivity as compared to methicillin-sensitive ones (MSSA).
2. The MIC values for *Pseudomonas aeruginosa* are between 2 and ≧64 mg/l, mostly at 4 mg/l. For one strain each of *Pseudomonas* species und *Acinetobacter baumannii*, lower MIC values were established.
3. The MIC values for *Escherichia coli* (cefotaxim-sensitive or -resistant) and for an isolate of *Enterobacter aerogenes* are above the measuring range (≧64 mg/l). For *Citrobacter freundii* (1 cefotaxim-sensitive isolate and 1 cefotaxim-resistant isolate each) and an isolate of *Klebsiella pneumoniae*, the MIC values are 4 and 8 mg/l, respectively.
4. The MIC values for *Candida albicans* are above the measuring range (≧64 mg/l) in all cases examined.

Evaluation of Results:

The MIC values of the protein isolated in Example 1 for *Staphylococcus aureus* are within the range of those of other *Staphylococcus*-specific antibiotics, such as vancomycin or mupirocin (pseudomonic acid A).

TABLE 4a

Individual values for the MIC determinations on the peptide of Example 1

| No. | Species | Identity No. | MIC (mg/l) |
|---|---|---|---|
| 1. | *S. aureus* | 29096894 | 0.25 |
| 2. | *S. aureus* | 29096979 | 0.25 |

TABLE 4a-continued

Individual values for the MIC determinations on the peptide of Example 1

| No. | Species | Identity No. | MIC (mg/l) |
|---|---|---|---|
| 3. | S. aureus | 29186557 | 0.25 |
| 4. | S. aureus | 290096544 | 0.25 |
| 5. | S. aureus | 290096573 | 0.5 |
| 6. | S. aureus | 291085630 | 0.25 |
| 7. | S. aureus | 291086167 | 0.5 |
| 8. | S. aureus | 293114034 | 0.25 |
| 9. | S. aureus | ATCC 25923 | 0.5 |
| 10. | S. aureus | ATCC 25923 | 0.125 |
| 11. | S. aureus | ATCC 29213 | 0.25 |
| 12. | S. aureus | ATCC 29213 | 0.25 |
| 13. | S. aureus (MRSA) | 29096530 | 0.5 |
| 14. | S. aureus (MRSA) | 29096578 | 0.25 |
| 15. | S. aureus (MRSA) | 29185647 | 0.25 |
| 16. | S. aureus (MRSA) | 29186257 | 0.125 |
| 17. | S. aureus (MRSA) | 290064272 | 0.125 |
| 18. | S. aureus (MRSA) | 290065119 | 0.125 |
| 19. | S. aureus (MRSA) | 290084217 | 0.25 |
| 20. | S. aureus (MRSA) | 290085795 | 0.125 |
| 21. | S. aureus (MRSA) | 291025969 | 0.125 |
| 22. | S. aureus (MRSA) | 291025990 | 0.125 |
| 23. | S. aureus (MRSA) | 291034340 | 0.25 |
| 24. | S. aureus (MRSA) | 291051784 | 0.125 |
| 25. | S. aureus (MRSA) | 291067083 | 0.125 |
| 26. | S. aureus (MRSA) | 292055432 | 0.25 |
| 27. | S. aureus (MRSA) | 292061054 | 0.25 |
| 28. | S. aureus (MRSA) | 292065865 | 0.125 |
| 29. | S. aureus (MRSA) | 292078001 | 0.5 |
| 30. | S. aureus (MRSA) | 293029965 | 0.25 |
| 31. | S. aureus (MRSA) | 293036524 | 0.5 |
| 32. | S. aureus (MRSA) | 293036526 | 0.125 |
| 33. | S. aureus (MRSA) | 293036839 | 0.25 |
| 34. | S. aureus (MRSA) | 293066533 | 0.125 |
| 35. | S. aureus (MRSA) | 293067107 | 0.125 |
| 36. | S. aureus (MRSA) | 293070769 | 0.125 |
| 37. | S. aureus (MRSA) | 293073166 | 0.125 |
| 38. | S. aureus (MRSA) | 293074729 | 0.125 |
| 39. | S. aureus (MRSA) | 293078957 | 0.125 |
| 40. | S. aureus (MRSA) | 293082503 | 0.125 |
| 41. | S. aureus (MRSA) | 293087915 | 0.125 |
| 42. | S. aureus (MRSA) | 293094792 | 0.125 |
| 43. | S. aureus (MRSA) | 293114029 | 0.5 |
| 44. | S. aureus (MRSA) | 294044109 | 0.25 |
| 45. | S. aureus (MRSA) | 294051030 | 0.125 |

TABLE 4b

Individual values for the MIC determinations on the peptide from Example 1

| No. | Species | Identity No. | MIC (mg/l) |
|---|---|---|---|
| 46. | E. coli | 29096769 | ≧64 |
| 47. | E. coli | 293115050 | ≧64 |
| 48. | E. coli | 293116474 | ≧64 |
| 49. | E. coli | ATCC 25922 | ≧64 |
| 50. | E. coli | ATCC 35218 | ≧64 |
| 51. | E. coli cefotaxim-res. | U-97-10432 | ≧64 |
| 52. | E. coli cefotaxim-res. | U-97-11088 | ≧64 |
| 53. | E. coli cefotaxim-res. | U-97-15538 | ≧64 |
| 54. | E. coli cefotaxim-res. | U-97-9689 | ≧64 |
| 55. | E. aerogenes | V2-92-33405 | ≧64 |
| 56. | C. freundii | U-93-13949 | 4 |
| 57. | C. freundii cefotaxim-res. | V1-97-10468 | 4 |
| 58. | K. pneumoniae | U-93-13367 | 8 |
| 59. | P. aeruginosa | 291087178 | 2 |
| 60. | P. aeruginosa | 291087279 | 16 |
| 61. | P. aeruginosa | 292084709 | 4 |
| 62. | P. aeruginosa | 292084851 | 4 |
| 63. | P. aeruginosa | 292084924 | ≧64 |
| 64. | P. aeruginosa | 293115624 | 8 |
| 65. | P. aeruginosa | 293115861 | 2 |
| 66. | P. aeruginosa | 293116074 | 4 |
| 67. | P. aeruginosa | 294082478 | 4 |
| 68. | P. aeruginosa | ATCC 27853 | 8 |
| 69. | P. aeruginosa | ATCC 27853 | 4 |
| 70. | P. aeruginosa | U-93-11944 | 32 |
| 71. | Pseudomonas spp. | U-98-5688 | 0.125 |
| 72. | A. baumannii | 29097133 | 2 |
| 73. | C. albicans | 291086916 | ≧64 |
| 74. | C. albicans | 291086918 | ≧64 |
| 75. | C. albicans | 291087192 | ≧64 |
| 76. | C. albicans | 292084887 | ≧64 |
| 77. | C. albicans | 294081971 | ≧64 |

TABLE 5

Summary of the results of MIC determinations for the protein isolated in Example 1

| | n | 0.06 | 0.12 | 0.25 | 0.5 | 1 | 2 | 4 | 8 | 16 | 32 | ≧64 |
|---|---|---|---|---|---|---|---|---|---|---|---|---|
| S. aureus (MSSA) | 12 | 0 | 1 | 8 | 3 | 0 | 0 | 0 | 0 | 0 | 0 | 0 |
| S. aureus (MRSA) | 33 | 0 | 20 | 9 | 4 | 0 | 0 | 0 | 0 | 0 | 0 | 0 |
| P. aeruginosa | 12 | 0 | 0 | 0 | 0 | 0 | 2 | 5 | 2 | 1 | 1 | 1 |
| Pseudomonas spp. | 1 | | 1 | | | | | | | | | |
| A. baumannii | 1 | 0 | 0 | 0 | 0 | 0 | 1 | 0 | 0 | 0 | 0 | 0 |
| E. coli | 9 | 0 | 0 | 0 | 0 | 0 | 0 | 0 | 0 | 0 | 0 | 9 |
| C. freundii | 2 | 0 | 0 | 0 | 0 | 0 | 0 | 2 | 0 | 0 | 0 | 0 |
| E. aerogenes | 1 | 0 | 0 | 0 | 0 | 0 | 0 | 0 | 0 | 0 | 0 | 1 |

TABLE 5-continued

Summary of the results of MIC determinations for the protein isolated in Example 1

|  | n | 0.06 | 0.12 | 0.25 | 0.5 | 1 | 2 | 4 | 8 | 16 | 32 | ≥64 |
|---|---|---|---|---|---|---|---|---|---|---|---|---|
| K. pneumoniae | 1 | 0 | 0 | 0 | 0 | 0 | 0 | 0 | 1 | 0 | 0 | 0 |
| C. albicans | 5 | 0 | 0 | 0 | 0 | 0 | 0 | 0 | 0 | 0 | 0 | 5 |

Example 5

Determination of Activity Against Malaria

For establishing the activity of the substance against malaria, 20 laboratory mice were infected with *Plasmodium bergi* according to standard methods. The injected mice were administered one single dose of the antibiotically active substance (50 mg/kg, non-purified) per intraperitoneal injection. The average survival time of the injected mice was determined in comparison with an untreated control group. The average lifetime of the malaria-infected mice is 4 days without treatment with the antibiotically active substance. The average lifetime of the mice treated with the antibiotically active substance is 6 days.

What is claimed is:

1. An isolated and purified peptide or protein comprising at least one of the sequences of SEQ ID NOs: 1 to 8 wherein said peptide or protein has antibiotic activity and wherein said peptide or protein is derived from the mucus of the foot sole of *Archachatina marginata*.

2. The isolated and purified peptide or protein according to claim 1, having molecular weight of more than 50 kDa.

3. The isolated and purified peptide or protein according to claim 1 which comprises all eight sequences of SEQ ID NOs: 1 to 8.

4. The isolated and purified peptide or protein according to claim 1, wherein said peptide or protein is glycosylated, ribosylated, acylated, phosphorylated, alkoxylated and/or amidated.

5. The isolated and purified peptide or protein according to claim 1, obtainable by recombinant techniques.

6. A therapeutic drug comprising the isolated and purified peptide or protein according to claim 1 wherein said drug is optionally formulated with a pharmaceutically acceptable carrier.

7. A foodstuff or feed containing the isolated and purified peptide or protein according to claim 1.

8. A method for treating infection caused by infectious pathogens in humans or animals comprising administering to said humans or animals an effective amount of the peptide or protein of claim 1.

9. The method according to claim 8, wherein the peptide or protein is in a form suitable for oral administration.

10. The method according to claim 8, wherein the peptide or protein is in a form suitable for intravenous administration or administration by application to the skin.

11. The method according to claim 8, wherein said infectious pathogens are bacteria, viruses or parasites.

* * * * *

```
                         SEQUENCE LISTING

<160> NUMBER OF SEQ ID NOS: 9

<210> SEQ ID NO 1
<211> LENGTH: 26
<212> TYPE: PRT
<213> ORGANISM: Archachatina marginata

<400> SEQUENCE: 1

Thr Asp Thr Gly Leu Tyr Leu Leu Glu Phe Leu His Thr Phe Thr Glu
 1               5                  10                  15

Asp Gly Ser Ile Gln Glu Thr Gly Ile Lys
            20                  25

<210> SEQ ID NO 2
<211> LENGTH: 19
<212> TYPE: PRT
<213> ORGANISM: Archachatina marginata

<400> SEQUENCE: 2

Val Ile Leu Ala Ile Pro Gln Ser Ala Leu Ile Glu Leu Asp Trp Lys
 1               5                  10                  15

Pro Leu Arg

<210> SEQ ID NO 3
<211> LENGTH: 20
<212> TYPE: PRT
<213> ORGANISM: Archachatina marginata

<400> SEQUENCE: 3

Gln Glu Asn Leu Asn Ala Gln Gly Glu Pro Ile Pro Gly Ser Ala Pro
 1               5                  10                  15

Gly Ala Asn Arg
            20

<210> SEQ ID NO 4
<211> LENGTH: 14
<212> TYPE: PRT
<213> ORGANISM: Archachatina marginata

<400> SEQUENCE: 4

Ala Gly Tyr His Cys Gln Tyr Ile Ile Tyr Ile Ile Gln Arg
 1               5                  10
```

```
<210> SEQ ID NO 5
<211> LENGTH: 12
<212> TYPE: PRT
<213> ORGANISM: Archachatina marginata

<400> SEQUENCE: 5

Gln Glu Gln Asn Gly Asn Leu Met Tyr Leu Asn Arg
 1               5                  10

<210> SEQ ID NO 6
<211> LENGTH: 13
<212> TYPE: PRT
<213> ORGANISM: Archachatina marginata

<400> SEQUENCE: 6

Asp Asn Thr Phe Pro Thr Thr Tyr Val Ala Glu Glu Lys
 1               5                  10

<210> SEQ ID NO 7
<211> LENGTH: 15
<212> TYPE: PRT
<213> ORGANISM: Archachatina marginata

<400> SEQUENCE: 7

Ile Phe Asp Asp Lys Pro Ile Pro Val Ala Gln Asp Glu Thr Lys
 1               5                  10                  15

<210> SEQ ID NO 8
<211> LENGTH: 17
<212> TYPE: PRT
<213> ORGANISM: Archachatina marginata

<400> SEQUENCE: 8

Thr Asn Ala Glu Tyr Glu Phe Leu Thr Thr Phe Arg Leu Asn Ala Tyr
 1               5                  10                  15

Lys

<210> SEQ ID NO 9
<211> LENGTH: 531
<212> TYPE: PRT
<213> ORGANISM: Achatina fulica

<400> SEQUENCE: 9

Met Leu Leu Leu Asn Ser Ala Leu Phe Ile Leu Cys Leu Val Cys Trp
 1               5                  10                  15

Leu Pro Gly Thr Ser Ser Ser Arg Val Leu Thr Arg Arg Glu Gly Pro
                20                  25                  30

Gln Cys Ser Arg Ser Val Asp Val Ala Val Val Gly Ala Gly Pro Ser
            35                  40                  45

Gly Thr Tyr Ser Ala Tyr Lys Leu Arg Asn Lys Gly Gln Thr Val Glu
        50                  55                  60

Leu Phe Glu Tyr Ser Asn Arg Ile Gly Gly Arg Leu Phe Thr Thr His
 65                  70                  75                  80

Leu Pro Asn Val Pro Asp Leu Asn Leu Glu Ser Gly Gly Met Arg Tyr
                85                  90                  95

Phe Lys Asn His His Lys Ile Phe Gly Val Leu Val Lys Glu Leu Asn
            100                 105                 110

Leu Ser Asn Lys Glu Phe Thr Glu Gly Phe Gly Lys Pro Gly Arg Thr
        115                 120                 125
```

-continued

```
Arg Phe Phe Ala Arg Gly Lys Ser Leu Thr Leu Glu Met Thr Ser
    130                 135                 140

Gly Asp Val Pro Tyr Asn Leu Ser Thr Glu Glu Lys Ala Asn Gln Ala
145                 150                 155                 160

Asn Leu Ala Gly Tyr Tyr Leu Lys Lys Leu Thr Gly Phe Asp Gly Glu
                165                 170                 175

Val Leu Thr Ile Pro Gln Ala Asn Lys Leu Glu Val Asp Asp Gly Arg
                180                 185                 190

Lys Leu Tyr Gln Leu Thr Val Asp Glu Ala Leu Asp Lys Val Gly Thr
                195                 200                 205

Pro Glu Gly Lys Glu Phe Leu Lys Ala Phe Ser Thr Gly Asn Thr Glu
    210                 215                 220

Phe Ile Glu Gly Val Ser Ala Val Asn Tyr Phe Leu Val Glu Leu Gly
225                 230                 235                 240

Glu Arg Glu Glu Glu Ile Leu Thr Leu Thr Asp Gly Met Ser Ala Leu
                245                 250                 255

Pro Gln Ala Leu Ala Asp Ala Phe Leu Lys Ser Ser Thr Ser His Ala
                260                 265                 270

Leu Thr Leu Asn Arg Lys Leu Gln Ser Leu Ser Lys Thr Asp Asn Gly
            275                 280                 285

Leu Tyr Leu Leu Glu Phe Leu Glu Thr Asn Thr His Glu Gly Tyr Thr
    290                 295                 300

Glu Glu Ser Asn Ile Thr Asp Leu Val Cys Ala Arg Lys Val Ile Leu
305                 310                 315                 320

Ala Ile Pro Gln Ser Ala Leu Ile His Leu Asp Trp Lys Pro Leu Arg
                325                 330                 335

Ser Glu Thr Val Asn Glu Ala Phe Asn Ala Val Lys Phe Ile Pro Thr
                340                 345                 350

Ser Lys Val Phe Leu Thr Phe Pro Thr Ala Trp Trp Leu Ser Asp Ala
            355                 360                 365

Val Lys Asn Pro Ala Phe Val Val Lys Ser Thr Ser Pro Phe Asn Gln
    370                 375                 380

Met Tyr Asp Trp Lys Ser Ser Asn Val Thr Gly Asp Ala Ala Met Ile
385                 390                 395                 400

Ala Ser Tyr Ala Asp Thr Ser Asp Thr Lys Phe Gln Glu Asn Leu Asn
                405                 410                 415

Ser Lys Gly Glu Leu Ile Pro Gly Ser Ala Pro Gly Ala Asn Arg Val
            420                 425                 430

Thr Val Ala Leu Lys Glu Glu Leu Leu Ser Gln Leu Ser Gln Ala Tyr
    435                 440                 445

Gly Ile Glu Arg Ser Asp Ile Pro Glu Pro Lys Ser Gly Thr Ser Gln
450                 455                 460

Phe Trp Ser Ser Tyr Pro Phe Glu Gly Asp Trp Thr Val Trp Lys Ala
465                 470                 475                 480

Gly Tyr His Cys Glu Tyr Thr Gln Tyr Ile Ile Glu Arg Pro Ser Leu
                485                 490                 495

Ile Asp Asp Val Phe Val Val Gly Ser Asp His Val Asn Cys Ile Glu
                500                 505                 510

Asn Ala Trp Thr Glu Ser Ala Phe Leu Ser Val Glu Asn Val Phe Glu
            515                 520                 525

Lys Tyr Phe
530
```